United States Patent [19]

Mester et al.

[11] Patent Number: 4,631,271
[45] Date of Patent: Dec. 23, 1986

[54] SEROTONIN-D-FRUCTOSE AND PHARMACEUTICAL COMPOSITION CONTAINING SAME

[76] Inventors: Làszlo Mester; Madeleine Mester nee Szadeczky-Kardoss, both of 3, Parc de Béarn, Saint-Cloud, France, 92210

[21] Appl. No.: 706,533

[22] Filed: Jul. 19, 1976

[30] Foreign Application Priority Data

Jul. 18, 1975 [FR] France .................. 75 22577

[51] Int. Cl.$^4$ .................. A61K 31/70; C07H 5/06
[52] U.S. Cl. .................. 514/23; 536/18.7
[58] Field of Search .................. 424/180; 536/18, 18.7; 514/23

[56] References Cited

U.S. PATENT DOCUMENTS 2,936,308  5/1960  Hodge .................. 536/18

Primary Examiner—Johnnie R. Brown

Attorney, Agent, or Firm—Weiser & Stapler

[57] ABSTRACT

The invention relates to new serotonin derivatives which form strong reducing agents. They can be represented by the formula:

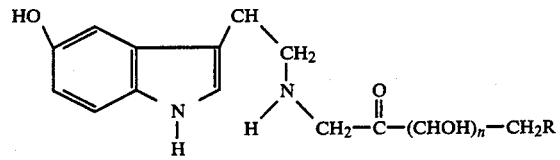

in which R represents a hydrogen atom or a hydroxyl group, and n when R represents a hydroxyl group is zero or one of the integers 1, 2 or 3, or when R represents a hydrogen atom is one of the integers 1, 2 or 3.

They form useful substitutes for serotonin, in all treatments of afflictions which call into play an excessive metabolization of serotonin.

3 Claims, 1 Drawing Figure

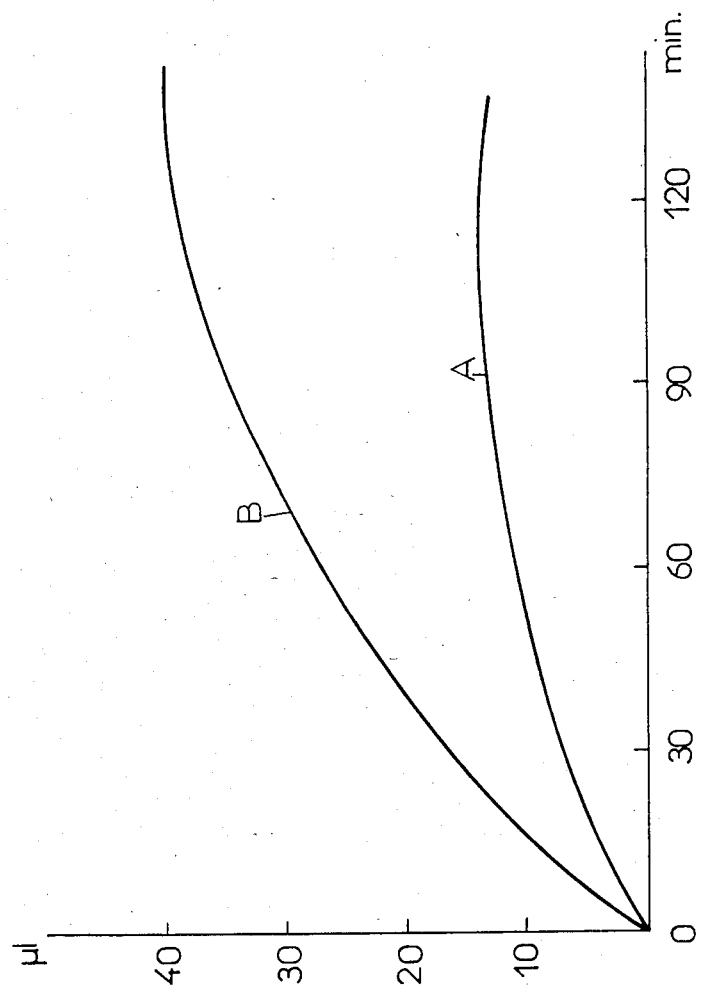

SEROTONIN-D-FRUCTOSE AND PHARMACEUTICAL COMPOSITION CONTAINING SAME

The invention concerns new derivatives of serotonin, a process for their preparation, and their use as active ingredients in the formulation of medicines.

Up to the present time a great many physiological, pharmacological and chemical investigations have been made into serotonin, otherwise known as 5-hydroxy-tryptamine (sometimes hereinafter designated by the abbreviation "5HT"), especially designed to try to elucidate the physiological role of this biogenic amine. It has in particular been established that a large number of pathological conditions manifest themselves in the patients afflicted by them inter alia by an irregularity in the metabolism of serotonin, an irregularity which manifests itself for instance by a reduction or on the contrary by an increase in the serotonin level in the serum or in the cerebro-spinal fluid.

The aforesaid investigations have already resulted in the preparation of a large number of substituted derivatives of serotonin. Amongst these products, only two glucidic derivatives have been described.

One of these derivatives is O-[β-D-glucopyranosyl]-serotonin of the formula:

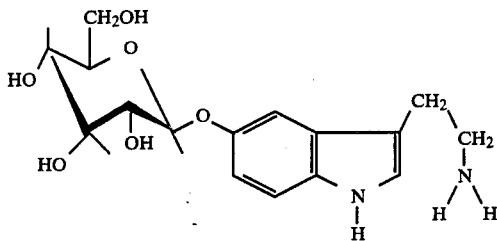

This compound displays an increased solubility in water as compared with serotonin, but otherwise has pharmacological properties very similar to the well known pharmacological properties of the O-ethers of serotonin.

The other known glucidic derivative of serotonin is the serotonin N-glucoside of the formula:

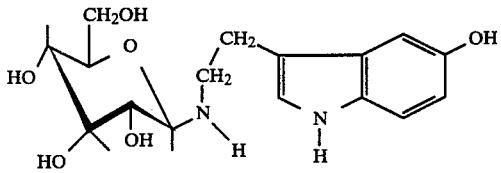

Interest in this compound is limited by reason of its ease of hydrolysis into 5-HT and into D-glucose in aqueous solution, even at ordinary temperatures.

It has however been found according to this invention that new glucidic derivatives of serotonin can be obtained which at one and the same time are stable, water-soluble and strong reducing agents, and which moreover possess a lesser sensitivity to the action of oxidizing agents.

The compounds according to the invention are formed as a serotonin in which one at least of the hydrogen atoms of the primary amine group in serotonin is substituted by a 1-desoxy-2-keto sugar. In particular, the invention concerns compounds which conform (when the glucidic group is in its open form) to the formula:

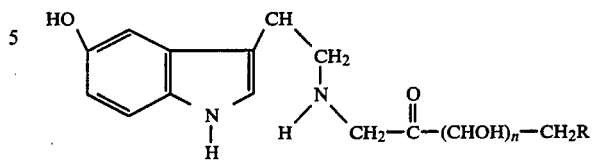

in which R represents a hydrogen atom or a hydroxyl group, and n when R represents a hydroxyl group is zero or one of the integers 1, 2 or 3, or when R represents a hydrogen atom is one of the integers 1, 2 or 3.

The preferred compounds according to the invention are those in which n when R represents a hydroxyl group is one of the integers 2 or 3, or when R represents a hydrogen atom is the integer 3.

The process according to the invention for preparing the new compounds, in which serotonin is reacted with the corresponding aldose of the formula:

$$RCH_2-(CHOH)_{n+1}-CHO$$

in which R and n have the previously-indicated meanings, is characterized by the introduction amongst the reactants or the reaction product thus obtained of a proton-donor agent under conditions appropriate to permit either the direct production starting from the aforesaid reactants of a 1-amino-1-desoxy-2-ketoso N-substituted derivative of serotonin, or the isomerization of the corresponding N-substituted aldosylamine, similarly derived from serotonin [and] perhaps at first formed starting from the aforesaid reactants, into the aforesaid 1-amino-2-ketoso N-substituted compound.

The previously-indicated conditions are specifically those which are employed in the processes in which an aldose is made to react with a primary amine, under conditions enabling one to achieve that which has been called "the Amadori rearrangement", that is to say the isomerization of the aldosylamine thus obtained into a 1-amino-1-desoxy-2-ketose. These conditions for the reaction, also called an Amadori-type reaction, are specifically described in "Methods in Carbohydrate Chemistry", Vol. 2, Acedemic Press, N.Y. 1963, page 99.

In a preferred method of carrying out the process according to the invention, the reaction is made to take place in the presence of an acid catalyst. The acid catalyst is specifically chosen from amongst those which possess an acidity sufficient to be able to confer a pH lying between about 3.5 and about 5.5 upon an aqueous solution. Equally it is employed specifically in the quantities which, if the medium used were aqueous, would enable this pH to be obtained. The acid can be any organic or mineral acid fulfilling the above-indicated condition, or acid-reacting salts. Serotonin itself can first be converted into such an acid-reacting salt.

Preferably the reaction is effected in an anhydrous solvent medium which is inert as regards the reactants, because of the risk of hydrolysis of the corresponding aldosylamine in the presence of water.

Advantageously the reaction is effected in an anhydrous alcoholic medium, such as methanol, ethanol, propanol or in some other solvent such as, for example, dioxan, dimethylformamide or acetonitrile.

Generally speaking, the amount of acid employed can be calculated very readily, for example by moistening an universal pH-indicator paper with the reaction medium and then putting a drop of water upon the paper thus moistened. The amount of acid used in the anhydrous medium is correct if the drop of water added to the paper indicator shows a pH lying between about 3.5 and about 5.5.

It is possible also to make use of other proton-donor agents, for example compounds containing an active methylene grouping ($=C-CH_2-C=$) for instance an ethyl malonate, 2,4-pentanedione, phenylacetone, diphenylmethane or malonic acid, in the presence of a catalytic amount of a secondary amine, and within an inert solvent.

In every case, the reaction can be carried out at a temperature lying between ambient and the reflux temperature of the solvent, and preferably at this latter temperature.

Generally speaking, it will be found that it is possible to operate under the conditions described in the previously-identified reference, or equally under those described in the Chapter by John E. Hodge entitled "The Amadori rearrangement", in "Advances in Carbohydrate Chemistry," Vol. 10, Acad. Press 1965, p. 169. Applied for example to serotonin and an aldose such as D-glucose, the above-indicated reaction conditions lead to a glucidic serotonin derivative derived from the ketose corresponding to the aldose used. For example, the reaction between serotonin and D-glucose is illustrated by the following chemical equation:

in the presence of the aldehyde into a tetrahydro-norharmane derivative of the formula

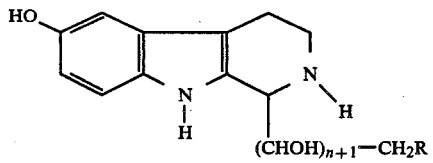

in which n and R have the previously-indicated meanings. A particularly advantageous acid fulfilling all the above-mentioned conditions is oxalic acid. Correspondingly the serotonin can as a first step be transformed into its oxalate.

Generally speaking, the same result is obtained by using polycarboxylic acids, specifically dicarboxylic or tricarboxylic acids. Advantageous representatives of these polycarboxylic acids are for example tartaric acid, maleic acid, malic acid, citric acid, etc. In every case, using these polycarboxylic acids, the products obtained are substantially free from derivatives of tetrahydronorharmane. At all events, it can be noted that if other acids are employed, for example mineral acids such as hydrochloric acid, it should be readily possible to separate the derivatives of tetrahydro-norharmane which possibly will be formed, bearing in mind their physical properties, such as their solubilities in solvents, which

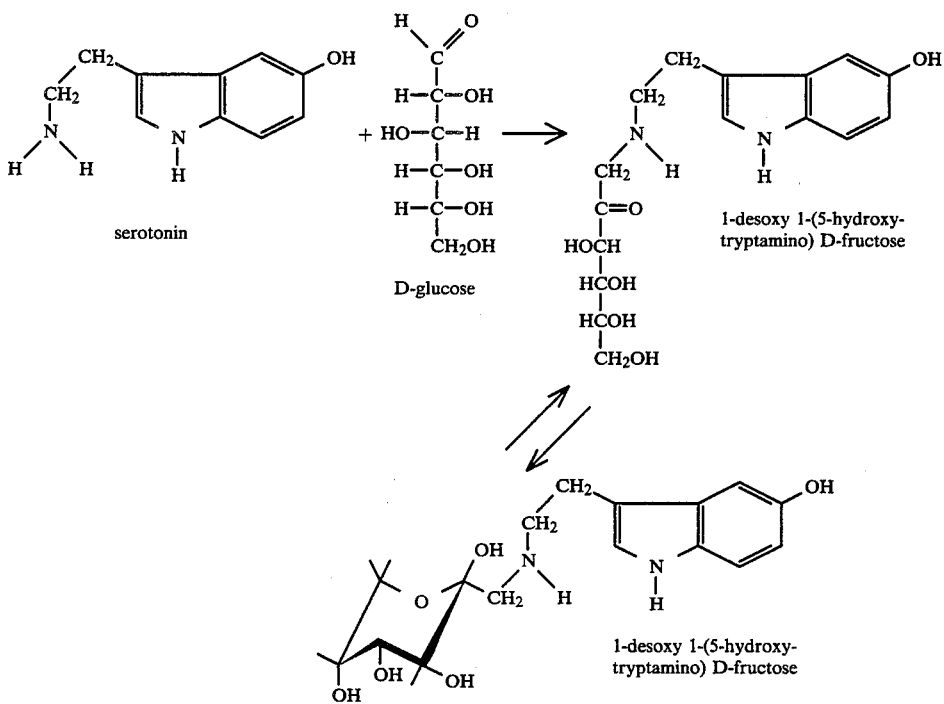

The same reaction carried out in a neutral medium would lead to the known, but unstable, compound of formula II herein above.

The presence of the proton-donor agent thus has a fundamental importance in the process according to the invention.

Although in principle one can employ the most diverse mineral or organic acids or acid salts of 5-HT, the acids or salts preferably employed are those which enable the serotonin to be stabilized in situ, especially against the risk of the partial transformation of the 5-HT are wholly different from those of the derivatives in question. Naturally, it is possible equally to use solutions of the corresponding salts of serotonin.

Amongst the aldoses principally used according to the invention there can be mentioned the following: glycerose, threose, erythrose, ribose, arabinose, xylose, lyxose, gulose, idose, glucose, mannose, galactose, talose, allose, altrose, rhamnose, fucose and epirhamnose (which in relation to each of them refers both to the D-series and to the L-series compound). Naturally, epimeric sugars which differ only in the configuration of the 2-carbon atom yield the same final products.

The compounds according to the invention have a marked reducing power. Specifically they reduce Tillmans reagent, that is to say 2,6-dichloro-phenol-indophenol (H. V. Euleur, H. Hasselquist, H. Wahlstam, Arkiv S. Kemi, 12, 85, (1957)) although the sugars from which they are derived are without effect on this reagent. Their reducing power against the TILLMANS reagent is generally equal to or greater than that of ascorbic acid.

The products according to the invention possess valuable pharmacological and therapeutic properties. In particular, on account of their marked reducing power, they are only slightly oxidized by the mono-amine oxidase (MAO) which is one of the agents involved in the metabolism of serotonin. Thus they can be employed to keep constant the amount of serotonin in the organism when the latter tends to be metabolised too rapidly. The products according to the invention exercise a mitogenic effect as regards cells which have been subjected to irradiation, when they are put in contact therewith. They are thus also effective as radiation-protecters.

Moreover, the compounds inhibit the platelet agregation induced by serotonin. From the fact of their anti-aggregant effect as regards the blood platelets, it is possible to envisage their use in the treatment of thromboses, specifically arterial thromboses.

Still further, they hinder the incorporation of serotonin in the platelets, hence their value in the treatment of shocks, which it is known are often accompanied by liberation of serotonin in the blood.

Other characteristics of the invention will appear in the course of the subsequent description, specifically the preparation of the compounds according to the invention and their pharmacological and physico-chemical properties.

EXAMPLE I

Preparation of the oxalate of
1-desoxy-1-(5-hydroxy-tryptamino) D-fructose (or 1-desoxy-1-([(5-hydroxy-3-indolyl)]-2-ethylamino) D-fructose)

0.532 g (0.002 mole) of serotonin oxalate and 0.360 g (0.002 mole) of anhydrous D-glucose (both of them manufactured by the firm Sigma Co., St. Louis) in 40 ml of absolute ethanol are taken to reflux for the period of 60 minutes. After cooling to ambient temperature, a pale yellow substance precipitates and is eliminated by filtration. On addition of 60 ml of anhydrous ethyl acetate, the major part of the product is caused to precipitate and, after filtration, one obtains 0.225 g of white or pale yellow micro-crystalline powder, which one can purify by recrystallisation starting with hot ethanol, with if necessary the addition of anhydrous ethyl acetate.

Characteristics of the oxalate of the product (of formula IV a or IVb) M.pt.—98°-102° C.; $[\alpha]_D^{20}$——14° (c=1, water) PERKIN-ELMER electronic polarimeter of type 141 CM).

The base is easily obtained by neutralization, specifically with calcium hydroxide, or by passing through a cation-exchange resin of the AMBERLITE or similar type.

Solubility:

The 1-desoxy-1-(5-hydroxy-tryptamino) D-fructose is easily soluble in water; it dissolves slowly in ethanol and is insoluble in ethyl acetate, ethyl ether and acetone.
Stability:

The 1-desoxy-1-(5-hydroxy-tryptamino) D-fructose is stable in aqueous solution. The oxalate does not undergo mutarotation.

EXAMPLE II

Under the same conditions the derivatives of serotonin have been prepared which are set out in the left-hand column of the table given below, in which equally there is shown the sugar employed as reactant, the melting point and the reducing power, measured against TILLMANS reagent, of the product obtained.

| Compound | Sugar used | Melting Point | Reducing Power |
|---|---|---|---|
| 1-desoxy-1-(5-hydroxy-tryptamino) D-tagatose | D-galactose | 95–96° | 3.2 H atoms |
| 1-desoxy-1-(5-hydroxy-tryptamino) D-ribulose | D-ribose | 110–112° | 3.5 H atoms |
| 1-desoxy-1-(5-hydroxy-tryptamino) D-xylulose | D-xylose | 98–99° | 2.4 H atoms |
| 1,6-didesoxy-1-(5-hydroxy-tryptamino) L-tagatose | L-fucose | 100–102° | 3.2 H atoms |
| 1,6-didesoxy-1-(5-hydroxy-tryptamino) L-fructose | L-rhamnose | 105–106° | 2.8 H atoms |

The sugars used have respectively the following formulae:

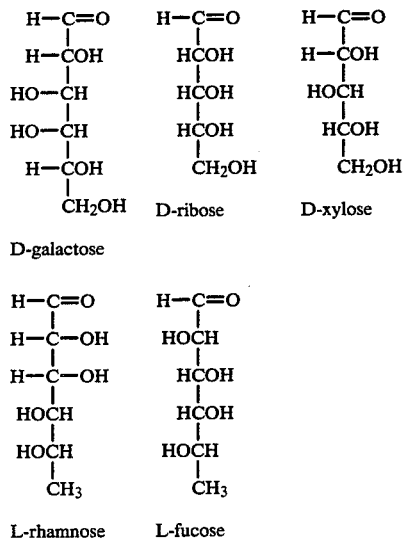

The results of the pharmacological investigations which follow, and which have been carried out with the oxalate of 1-desoxy-1-(5-hydroxytryptamino) D-fructose, are representative of the properties of the compounds in this family of new products, as defined hereinabove.

Pharmacological Investigation:

The pharmacological tests have been carried out with the oxalate of 1-desoxy-1-(5-hydroxy-tryptamino) D-fructose, identified hereinafter by the abbreviation "5-HTF" and equally hereinafter called "fructoserotonin", and with the oxalate of serotonin (5-HT) as a comparison product.

I. Behaviour as against monoamine-oxydase (MAO)

1. MAO of the brain of the rat:

Albino rats fed ad libitum and weighing about 100-150 g were sacrificed by decapitation. The brain was rapidly excised, and homogenized with the aid of a homogenizer (of the POTTER-ELVEHJEM type) in a 0.25M solution of sucrose cooled with ice. The brain homogenate thus obtained was diluted to 15% (weight per volume) with a 0.25M solution of sucrose and the suspension thus obtained was used as the source of MAO.

The MAO activity of the brain homogenate of the rat was evaluated by the usual manometric WARBURG technique, employing 5-HT and 5-HTF as substrates.

The adsorption of oxygen during the oxydative desamination of the 5-HT and of the 5-HTF was employed as the index of enzymatic activity. The reaction mixture contained 66 mM of phosphate buffer (pH 7.4), 10 mM of 5-HT or of 5-HTF, and a proportion of homogenate equivalent to 100 mg of fresh tissue. The enzymatic system was incubated at 27° C., under a gaseous phase of oxygen for two hours. The readings concerning the adsorption of oxygen were taken every 30 minutes. The results obtained were set out in FIG. 1, which gives the volumes of oxygen absorbed in microliters (along the ordinate) as a function of time in minutes (along the abscissa) by the medium containing the fructoserotonin (curve A).

Examination of this curve makes it possible to say that the consumption of oxygen by MAO in the presence of 5-HTF is less significant than in the presence of 5-HT, that is to say that 5-HTF is less easily metabolised by the MAO than 5-HT.

2. MAO rat liver:

Albino rats kept in the animal collection were sacrificed by decapitation. The liver was extracted and homogenized in a 0.25M solution of sucrose, in the cold, with the aid of the POTTER-ELVEHJEM homogeniser. The homogenate was diluted to 10% (weight by volume) with a 0.25M solution of sucrose, centrifuged at 750 g for a period of 20 minutes in a refrigerated centrifuge. After elimination of the residue, the supernatent liquid (750 g) was centrifuged at 15,000 g, for a period of 30 minutes in the cold, and the residue (mitochondric fraction) was dispersed in a 0.25M solution of sucrose and re-separated at 15,000 g for a period of 30 minutes. The residue was suspended in a 0.25M solution of sucrose to give a mitochondic preparation of 10% (in weight per volume).

The activity of the MAO on 5-HT or 5-HTF was determined by the PARMAR method (BIOCHEM. Pharmacol., 15, 1497 (1966)). The test mixture contained: 0.5 ml of phosphate buffer, 0.1M at pH=7.4, 0.2 ml of mitochondric preparation, variable concentrations of 5-HT and of 5-HTF (1.25 to 15 mM) and water to yield a total volume of 1.0 ml. The reaction was initiated by the addition of the substrate. The test tubes were incubated at 37° C. for 30 minutes. The control test tubes contained all the ingredients except the substrate, which was added when the reaction was interrupted by addition of 1.0 ml of 10% trichloroacetic acid. The test tubes were centrifuged and suitable predetermined aliquot fractions were taken, in order to evaluate the serotonin activity by the UDENFRIED, WEISSBACH and CLARK method (J Biol. Chem., 915, 337 (1955)).

Results:

Effect of the concentration of the substrate and specificity of the substrate.

Using concentrations from 1.25 to 15 mM of 5-HT or of 5-HTF, curves were obtained relative to the activity of the substrate having a hyperbolic outline corresponding to a classical kinetic of the MICHAELIS type. The MICHAELIS constant (Km) determined in a manner in itself known is, for 5-HTF, one and a half times higher than that of 5-HT, which indicates an affinity for MAO of 5-HTF lower than that of 5-HT. Consequently it can be deduced that MAO metabolizes 5-HT more rapidly than 5-HTF. The results obtained appear in the following table:

| Concentration of Substrate (S) mM | $\frac{1}{S}$ mM | 5-HT Speed of Reaction | $\frac{1}{V}$ | 5-HTF Speed of Reaction | $\frac{1}{V}$ |
|---|---|---|---|---|---|
| 1   1.25  | 0.800 | 0.48 | 2.080 | 0.360 | 2.77 |
| 2   2.50  | 0.400 | 0.78 | 1.280 | 0.720 | 1.39 |
| 3   3.75  | 0.266 | 1.68 | 0.595 | 0.960 | 1.04 |
| 4   5.00  | 0.200 | 1.92 | 0.520 | 1.56  | 0.34 |
| 5   7.50  | 0.133 | 2.76 | 0.360 | 2.04  | 0.45 |
| 6   10.00 | 0.100 | 3.36 | 0.300 | 2.40  | 0.41 |
| 7   15.00 | 0.066 | 3.84 | 0.260 | 2.64  | 0.37 |

Finally it will be noted that 5-HTF exerts an action on the uterus of the rat one hundred times less strong than that of 5-HT itself.

This activity of 5-HTF, like that of serotonin itself, is inhibited by methylsergide.

The tests which are set out above consequently put in evidence the fact that 5-HTF is distinctly less easily metabolized than 5-HT, notably in an oxidizing medium, under conditions which can be regarded as representative of those which prevail in the organism. 5-HT is thus capable of constituting a useful substitute for serotonin, in all treatments of afflictions which call into play an excessive oxidizing metabolization of serotonin.

TESTS IN VITRO AS REGARDS PLATELET AGGREGATION

Fructoserotonin was tested on plasma rich in platelets, in an agrogometer of the BRISTOL/HAMILTON (Canada) type. This apparatus makes it possible to detect platelet aggregations by photometry, with the help of an automatic recorder. Plasma rich in platelets is of low transparency. When there is aggregation, it becomes clearer and light can pass through it.

1. Action of 5-HTF used alone:

5-HTF can bring about an aggregation of platelets, starting from sufficiently elevated concentration thresholds. This however is not the case with the dosages which were employed in the following experiments:

To 0.3 ml of plasma rich in platelets, there are added 90 microliters of MICHAELIS (STAGO, France) buffer. The mixture is agitated at 37° C. for 2 minutes. 10 microliters are added of a solution of fructoserotonin at a concentration of $4.10^{-3}$ which gives a final concentration of $1.10^{-4}$.

2. Action of 5-HT:

Operating under the same conditions as in 1. above, except for the replacement of 5-HTF by 5-HT, a strong platelet aggregation is obtained.

3. Inhibition of the platelet aggregation caused by 5-HTF:

0.3 ml of plasma rich in platelets, 80 microliters of buffer, 10 microliters of fructoserotonin at a concentration of $4.10^{-3}$ were incubated, without agitation, at 37°

C. for 3 minutes. After 2 minutes of agitation, serotonin is added to a concentration of $4.10^{-3}$. Aggregation is not established. Aggregation by serotonin is completely inhibited.

It is possible to put forward the hypothesis that the absence of the platelet aggregation induced by 5-HT, in the presence of 5-HTF, at a dose at which the latter does not itself induce a platelet aggregation, can be attributed to the 5-HTF occupying the receptive sites on the platelet membrane upon which normally serotonin attaches itself, leading then to the platelet aggregation. The effect of the inhibition of the aggregation of the platelets which is exerted by the glucidic derivatives of serotonin, of the "Amadori products" type, thus make these products useful in the treatment of afflictions caused by platelet aggregation, notably thrombolytic states and more especially states of shock, which as is well known involve a liberation of serotonin which tends to produce an aggregation of platelets.

RADIATION-PROTECTIVE EFFECT OF 5-HTF

The incorporation of 5-HTF in cultures of Ehrlich dropsy cells, of mouse marrow strain cells, and of mouse thymus cells is reflected after irradiation, by a more rapid mitosis in cultures containing 5-HTF than that observed in cultures of control cells, held under the same conditions of incubation, suggesting the possible utilization of 5-HT as the active ingredient of a medicament for the prevention or the protection of patients submitted to radio therapy against the damaging effects of the rays.

It should finally be noted that 5-HTF is perfectly inocuous, by virtue of the very nature of its composition, since it is constituted as a glucidic derivative of serotonin. It is in fact known that it is a general rule that glucidic derivatives of any given compound never in general have a toxicity greater than that of the compound itself. This general rule holds good in the particular case for the glucidic derivatives of serotonin.

The other glucidic derivatives of serotonin, specifically those which are the subject of Example II hereinbefore, display behaviours completely analogous to those of 5-HTF, in particular in the pharmacological tests whose results specifically as regards 5-HTF were reported hereinabove.

Naturally the invention equally concerns the salts, and more especially the physiologically-acceptable salts of the derivatives according to the invention. These salts can be obtained by any method known per se, no matter whether these are by way of double decomposition reactions (for example the reaction of the oxalate of a glucidic derivative of serotonin with a calcium salt whose anion is to replace the oxalate ion) or by passing through the intermediary of the free base.

The products according to the invention or their physiologically-acceptable salts can constitute the active ingredients of medicaments administratable by all routes, notably by the oral route (given in particular their resistance to acids, which enables them to break through the gastric barrier), by the rectal route or by the parenteral route.

They can be associated with any pharmaceutically-acceptable solid or liquid excipients, permitting administration by the oral route; they can be associated with any vehicles permitting their administration by the rectal route, of the glyceride or analogous kind, notably those susceptible to softening or melting at a temperature lying between ambient temperature and 37° C.; or they can be dissolved or suspended in any injectable vehicle, notably in isotonic, sterile, aqueous injectable solutions.

As goes without saying, and as appears moreover already from what has gone before, the invention is in no way limited to those of its methods of application and achievement more particularly set forth; on the contrary it covers all possible variations.

We claim:

1. The serotonin derivative which is 1-desoxyl-1-(5-hydroxy-tryptamino) D-fructose, and its water-soluble physiologically acceptable salts.

2. A pharmaceutical composition which comprises a physiologically effective amount of the serotonin derivative of claim 1, and a physiologically acceptable carrier.

3. The stable aqueous solution of the compound of claim 1.

* * * * *